US009987409B2

(12) United States Patent
Mabuchi et al.

(10) Patent No.: US 9,987,409 B2
(45) Date of Patent: *Jun. 5, 2018

(54) BLOOD PURIFIER AND BLOOD PURIFIER PACKAGE

(71) Applicant: Nipro Corporation, Osaka-shi, Osaka (JP)

(72) Inventors: Kimihiro Mabuchi, Otsu (JP); Noriko Monden, Otsu (JP); Noriaki Kato, Otsu (JP); Yuuki Hatakeyama, Osaka (JP); Takashi Sunohara, Osaka (JP); Toshiaki Masuda, Osaka (JP)

(73) Assignee: NIPRO CORPORATION, Osaka (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/722,756

(22) Filed: May 27, 2015

(65) Prior Publication Data

US 2015/0258264 A1  Sep. 17, 2015

Related U.S. Application Data

(63) Continuation of application No. 11/577,209, filed as application No. PCT/JP2005/018861 on Oct. 13, 2005, now Pat. No. 9,050,410.

(30) Foreign Application Priority Data

Oct. 15, 2004 (JP) .................................. 2004-301771

(51) Int. Cl.
| *B01D 39/00* | (2006.01) |
| *B01D 39/14* | (2006.01) |
| *A61M 1/16* | (2006.01) |
| *A61L 2/08* | (2006.01) |
| *B01D 65/02* | (2006.01) |
| *B01D 67/00* | (2006.01) |
| *B01D 71/68* | (2006.01) |
| *B01D 69/08* | (2006.01) |

(52) U.S. Cl.
CPC ............ *A61M 1/168* (2013.01); *A61L 2/087* (2013.01); *A61M 1/16* (2013.01); *B01D 65/022* (2013.01); *B01D 67/0011* (2013.01); *B01D 67/0097* (2013.01); *B01D 69/08* (2013.01); *B01D 71/68* (2013.01); *A61L 2202/22* (2013.01); *B01D 2321/34* (2013.01); *B01D 2323/34* (2013.01); *B01D 2325/36* (2013.01); *B01D 2325/38* (2013.01)

(58) Field of Classification Search
CPC ...... A61L 2202/22; A61L 2/087; A61M 1/16; A61M 1/168; B01D 2321/34; B01D 2323/34; B01D 2325/36; B01D 2325/38; B01D 65/022; B01D 67/0011; B01D 67/0097; B01D 71/68

USPC .......... 210/500, 321.8, 500.41, 500.23, 646, 210/321.79, 321.81, 321.88, 433.1, 650; 264/41; 426/118

See application file for complete search history.

(56) References Cited

U.S. PATENT DOCUMENTS

| 4,813,210 A | 3/1989 | Masuda et al. |
| 5,436,068 A | 7/1995 | Kobayashi et al. |
| 5,441,488 A | 8/1995 | Shimura et al. |
| 5,641,450 A | 6/1997 | Kobayashi et al. |
| 5,881,534 A | 3/1999 | Ahlqvist et al. |
| 5,889,093 A | 3/1999 | Hatakeyama et al. |
| 6,133,361 A | 10/2000 | Hatakeyama et al. |
| 6,605,218 B2 | 8/2003 | Kozawa et al. |
| 6,776,912 B2 | 8/2004 | Baurmeister |
| 7,442,302 B2 | 10/2008 | Mabuchi et al. |
| 2001/0004976 A1 | 6/2001 | Kozawa et al. |
| 2002/0051730 A1 | 5/2002 | Bodnar et al. |
| 2005/0063859 A1 | 3/2005 | Masuda et al. |
| 2005/0072731 A1 | 4/2005 | Kozawa et al. |
| 2006/0205309 A1 | 9/2006 | Mabuchi et al. |
| 2007/0114167 A1 | 5/2007 | Mabuchi et al. |
| 2007/0187320 A1 | 8/2007 | Mabuchi et al. |
| 2007/0199891 A1 | 8/2007 | Mabuchi et al. |
| 2008/0000830 A1 | 1/2008 | Mabuchi et al. |
| 2008/0044643 A1 | 2/2008 | Yokota et al. |
| 2008/0067122 A1 | 3/2008 | Mabuchi et al. |
| 2008/0087599 A1 | 4/2008 | Mabuchi et al. |
| 2008/0142434 A1 | 6/2008 | Mabuchi et al. |

FOREIGN PATENT DOCUMENTS

| EP | 0 218 003 A1 | 4/1987 |
| JP | 55-23620 B2 | 6/1980 |
| JP | 58-134840 A | 8/1983 |
| JP | 62-074364 A | 4/1987 |
| JP | 62-204754 A | 9/1987 |
| JP | 63-111878 A | 5/1988 |
| JP | 04-300636 A | 10/1992 |
| JP | 06-285152 A | 10/1994 |
| JP | 08-168524 A | 7/1996 |
| JP | 10-165773 A | 6/1998 |
| JP | 10-309427 A | 11/1998 |

(Continued)

OTHER PUBLICATIONS

U.S. Appl. No. 11/721,766, filed Jan. 25, 2008.

(Continued)

*Primary Examiner* — Dirk Bass
(74) *Attorney, Agent, or Firm* — Leydig, Voit & Mayer, Ltd.

(57) ABSTRACT

The invention provides a blood purifier which shows a decreased amount of hydrogen peroxide extracted from its selectively permeable separation membranes, and thus is highly reliable in its safety in use for hemecatharysis. The blood purifier comprises selectively permeable separation membranes as a main component and is characterized in that the amount of hydrogen peroxide which is extracted from the selectively permeable separation membrane removed from the blood purifier after 3 months or longer has passed since the sterilization of the blood purifier by exposure to a radioactive ray and/or an electron ray is not larger than 10 ppm.

7 Claims, No Drawings

(56) References Cited

FOREIGN PATENT DOCUMENTS

| | | | |
|---|---|---|---|
| JP | 2000-225326 A | 8/2000 |
| JP | 2000-288085 A | 10/2000 |
| JP | 2001-170167 A | 6/2001 |
| JP | 2001-205057 A | 7/2001 |
| JP | 2003-245526 A | 9/2003 |
| JP | 2004-195380 A | 7/2004 |
| WO | WO 1995/033651 A1 | 12/1995 |
| WO | WO 1998/058842 A1 | 12/1998 |
| WO | WO 2003/039721 A1 | 5/2003 |

OTHER PUBLICATIONS

U.S. Appl. No. 11/577,235, filed Dec. 12, 2007.
U.S. Appl. No. 11/573,339, filed Aug. 29, 2007.
U.S. Appl. No. 11/573,333, filed Aug. 29, 2007.
U.S. Appl. No. 10/582,052, filed Nov. 22, 2006.
U.S. Appl. No. 10/599,167, filed Sep. 21, 2006.
U.S. Appl. No. 10/559,544, filed Mar. 29, 2006.
U.S. Appl. No. 10/559,398, filed Dec. 5, 2005.
U.S. Appl. No. 10/947,323, filed Sep. 23, 2004.
U.S. Appl. No. 11/577,209, filed Nov. 20, 2007.
Japanese Patent Office, International Search Report in International Patent Application No. PCT/JP2005/018861 (dated Jan. 17, 2006).
Japanese Patent Office, International Preliminary Report on Patentability in International Patent Application No. PCT/JP2005/018861 (dated Apr. 17, 2007).
Japanese Patent Office, Office Action in Japanese Patent Application No. 2004-301771 (dated Jul. 27, 2010).
Japanese Patent Office, International Search Report in International Patent Application No. PCT/JP2005/018862 (dated Jan. 24, 2006).
Japanese Patent Office, International Preliminary Report on Patentability in International Patent Application No. PCT/JP2005/018862 (dated Apr. 17, 2007).
European Patent Office, European Search Report in European Patent Application No. EP 045793649 (dated May 14, 2008).
Japanese Patent Office, International Search Report in International Patent Application No. PCT/JP2005/023337 (dated Jan. 17, 2006).
Japanese Patent Office, International Preliminary Report on Patentability in International Patent Application No. PCT/JP2005/023337 (dated Jun. 26, 2007).
European Patent Office, Extended European Search Report in European Application No. 05793644.5 (dated Sep. 18, 2013).
European Patent Office, Extended European Search Report in European Application No. 05820333.2 (dated Nov. 19, 2014).

BLOOD PURIFIER AND BLOOD PURIFIER PACKAGE

CROSS-REFERENCE TO RELATED APPLICATIONS

This patent application is a continuation of copending U.S. patent application Ser. No. 11/577,209, filed on Nov. 20, 2007, which is the U.S. national phase of International Patent Application No. PCT/JP2005/018861, filed Oct. 13, 2005, which claims the benefit of Japanese Patent Application No. 2004-301771, filed on Oct. 15, 2004, which are incorporated by reference in their entireties herein.

TECHNICAL FIELD

The present invention relates to a blood purifier which is highly reliable in safety and a package of the same. Particularly, the present invention pertains to a blood purifier which shows a decreased amount of hydrogen peroxide extracted from its selectively permeable separation membranes, and a package of the same.

BACKGROUND OF THE INVENTION

In hemocatharsis for therapy of renal failure, etc., blood purifiers such as hemodialyzers, hemofilters and hemodiafilters, comprising dialyzing membranes or ultrafilter membranes as separators, are widely used in order to remove urinal toxic substances and waste products in blood. The dialyzing membranes and the ultrafilter membranes as separators are made of natural materials such as cellulose or the derivatives thereof (e.g., cellulose diacetate, cellulose triacetate, etc.) or synthetic polymers such as polysulfone, polymethyl methacrylate, polyacrylonitrile, etc. The importance of blood purifiers comprising the hollow fiber type selectively permeable separation membranes as separators is very high in the field of dialyzers, in view of the advantages such as the reduction of the amount of extracorporeal circulated blood, high efficiency of removing undesired substances in blood, and high productivity of manufacturing modules.

To use the above blood purifiers as artificial kidney dialyzers, it is needed to completely sterilize the blood purifiers before use. For this sterilization, formalin, ethylene oxide gas, high-pressure steam, or exposure to radioactive rays such as a γ-ray or electron rays is employed, and each of these means exhibits its individual effect. Among those, the sterilization by exposure to radioactive rays or electronic rays is preferably employed because a subject in a package as it is can be directly subjected to a sterilization treatment, and because the sterilization effect of this method is high.

However, it is known that selectively permeable separation membranes for use in such a blood purifier and an adhesive, etc. for use in fixing such membranes tend to deteriorate due to the exposure to radioactive rays or electronic rays. Under such a circumstance, there are proposed methods for sterilization while preventing the deterioration of membranes, adhesives, etc. For example, a method of inhibiting the deterioration of hollow fiber membranes due to exposure to γ-ray by maintaining the hollow fiber membranes in a wet state (cf. Patent Literature 1). However, this method has the following problems: the weight of the blood purifier inevitably increases since it is needed to maintain the hollow fiber membranes in a wet state, which leads to disadvantages in the transport and handling thereof; or the hollow fiber membranes tend to burst or are damaged under such severely cold conditions that the water used to wet the membranes is frozen. Further, the preparation of a large amount of sterilized water is one of factors for higher cost. Furthermore, there is a possible danger of proliferation of bacteria in a very short time interval between the completion of packaging and the starting of sterilization, since the hollow fiber membranes are intentionally maintained in a wet state which facilitates the proliferation of bacteria. As a result, it takes a long time in completely sterilizing the blood purifier thus manufactured, and undesirably, such a disadvantage induces a higher cost and poor safety.

To avoid the wet state of hollow fiber membranes and to inhibit the deterioration thereof due to exposure to radioactive rays, a sterilization-protective agent such as glycerin, polyethylene glycol or the like is contained in the hollow fiber membranes, and such hollow fiber membranes are exposed to γ-ray with their moisture content maintained at not higher than 30% (cf. Patent Literature 2). However, this method suffers from the following problems because of the protective agent contained in the hollow fiber membranes: that is, it is difficult to suppress the moisture content of the hollow fiber membranes lower; the protective agent tends to deteriorate due to the exposure to γ-ray; and it is needed to remove the protective agent by washing the hollow fiber membranes before use.

There is disclosed a method of solving the above-discussed problems (cf. Patent Literature 3). According to this method, hollow fiber membranes of which the moisture content is not higher than 5% are exposed to a radioactive ray under an ambient atmosphere of not higher than 40% RH for their sterilization. This method is effective to solve the foregoing problems and to clear a criterion for the test regulated in the approval standards for manufacturing dialyzer type artificial kidney devices: that is, the UV absorbance (at a wavelength of 220 to 350 nm) of an extract from hollow fiber membranes is lower than 0.1. However, this Patent Literature does not describe or suggest about the following problems: some influences of the ambient atmosphere (oxygen and water) around the hollow fiber membranes (or hollow fiber membrane modules) during the storage thereof act to deteriorate (or oxidize and decompose) the materials of the hollow fiber membranes; and the UV absorbance of the extract (or the amount of eluate) from the hollow fiber membranes tends to increase with time because of the deterioration of the materials of the hollow fiber membranes.

In the meantime, there is disclosed a method of suppressing the insoluble component of the materials of hollow fiber membranes to not higher than 10 wt. % by exposing the hollow fiber membranes to γ-ray with their moisture content kept at not higher than 10 wt. % (cf. Patent Literature 4). It is described in this Patent Literature that the amount of a hydrophilic polymer which is extracted from membranes using a 40% aqueous ethanol solution is not larger than 2.0 mg/m$^2$ per one m$^2$ of the area of the membranes on their sides in contact with a treated fluid.

The present inventors have intensively studied in order to improve the above-described sterilization method by way of exposure to a radioactive ray or an electron ray. As a result, they have found that the sterilization method by way of exposure to a radioactive ray or an electron ray induces the formation of hydrogen peroxide which can not be detected by the above UV absorption spectrometry. As a result of this finding, it is found that a hydrophilic polymer is extracted by the above extraction method. While the mechanism of forming hydrogen peroxide is unknown, the following can be supposed: the deterioration of the base materials of selectively permeable separation membranes is induced by the presence of hydrogen peroxide; hydrogen oxide has an influence on the increase of the amount of an eluate from the membranes, which is detected by the above UV absorbance and which tends to increase after the exposure to the radioactive ray or the electron ray; and the amount of hydrogen peroxide itself tends to increase with time, which further accelerates the deterioration of the materials to thereby increase the amount of the above known extract from the membranes. Accordingly, it is known that strict control is needed for the exposure of hollow fiber membranes to the radioactive ray or the electron ray and for the following storage of the hollow fiber membranes in order to ensure safety as a blood purifier.

In the meantime, Patent Literature 3 and Patent Literature 4 do not refer to the formation of hydrogen peroxide during the storage of hollow fiber membranes and hollow fiber membrane modules, or to an absorbance (or an eluate) which tends to increase with time after the exposure to γ-ray, or to an increase in amount of a hydrophilic polymer (polyvinyl pyrrolidone) in an extract from the membranes using a 40% aqueous ethanol solution. Patent Literature 4 does not refer to the influence of a humidity of an ambient atmosphere around the hollow fiber membranes, on the deterioration of the materials of the hollow fiber membranes.

To avoid the deterioration of the base materials of medical devices attributed to the presence of oxygen, it is known that the medical devices are sealed in packaging media made of oxygen impermeable materials, together with oxygen scavengers, and are then exposed to radioactive rays, and it is also disclosed that this method can be applied to blood purifiers (cf. Patent Literature 5, Patent Literature 6 and Patent Literature 7).

The deterioration of hollow fiber membranes because of the above radiation exposure in the presence of the oxygen scavenger is accompanied by odors (described in Patent Literature 5), a decrease in strength or dialyzing performance of the base materials (described in Patent Literature 6) or a decrease in strength of the base materials or formation of aldehydes (described in Patent Literature 7). However, any of these Patent Literatures does not refer to an increase in amount of the above extracts. Further, any of these Patent Literatures refers to the oxygen concentration in the package under the radiation exposure, but not to the importance of the moisture content of the selectively permeable separation membranes and the humidity of the ambient atmosphere.

Patent Literatures 8 and 9 disclose hollow fiber membrane modules which show decreased amounts of hydrophilic polymers and which use no filling fluid, by displacing the internal atmospheres of the hollow fiber membrane modules with inert gases. However, the oxygen concentrations in atmospheres for the sterilization of the hollow fiber membrane modules are high, and therefore, it is impossible to completely inhibit the deterioration and decomposition of the materials of the hollow fiber membranes under the radiation exposures. Consequently, the amounts of eluates from the hollow fiber membrane modules can not be reduced, and there arises a further problem that the biocompatibility of the membranes becomes poor since the materials of the membranes are crosslinked by the radiation exposures.

Patent Literature 10 discloses a technique of sealing a fluid separation membrane module in a packaging bag. According to this Patent Literature, the fluid separation membrane module and the packaging bag are filled with deairing water before the storage of the fluid separation membrane module in the packaging bag, and the packaging bag is made of a material capable of shutting out an air so as to seal the membrane module. This technique is intended to prevent the fluid separation membranes from partially drying due to the gasification of the air which is caused because of a change in the temperature of the atmosphere during the storage of the fluid separation membranes. However, in this technique, no attention is paid to an increased transport cost attributed to the increased weight of the package or to the proliferation of bacteria during the storage of the membranes.

Patent Literature 1: JP-B-55-23620
Patent Literature 2: JP-A-6-285152
Patent Literature 3: JP-A-2000-288085
Patent Literature 4: JP-A-2001-205057
Patent Literature 5: JP-A-62-74364
Patent Literature 6: JP-A-62-204754
Patent Literature 7: WO98/58842
Patent Literature 8: JP-A-2001-170167
Patent Literature 9: JP-A-2003-245526
Patent Literature 10: JP-A-2004-195380

DISCLOSURE OF THE INVENTION

Problems to be Solved by the Invention

Objects of the present invention are to provide a blood purifier sterilized by exposure to a radioactive ray or an electron ray, particularly a high safety blood purifier for hemocatharsis, which shows less hydrogen peroxide extracted from its selectively permeable separation membranes, and to provide a blood purifier package.

Means for Solving the Problems

That is, the present invention relates to a blood purifier which comprises selectively permeable separation membranes as a main component, and which is characterized in that the amount of hydrogen peroxide extracted from the selectively permeable separation membranes which are removed from the blood purifier after 3 months or longer has passed since the sterilization of the blood purifier by exposure to a radioactive ray and/or an electron ray is not larger than 10 ppm.

Effect of the Invention

The blood purifier of the present invention, sterilized by exposure to a radioactive ray and/or an electron ray, shows less amount of extracted hydrogen peroxide which is found after the exposure to the radioactive ray and/or the electron ray, or which tends to change with time after such exposure. Further, the formation of various extracted substances attributed to the deterioration of the selectively permeable separation membranes due to the hydrogen peroxide can be inhibited, and thus, the reliability in safety of the blood purifier for use in hemocatharsis is markedly improved.

BEST MODES FOR CARRYING OUT THE INVENTION

Preferably, the selectively permeable separation membranes to be used in the present invention comprise a hydrophobic polymer containing a hydrophilic polymer. As raw materials for the hydrophobic polymer to be used in the present invention, there are preferably used cellulose-based polymers such as regenerated cellulose, cellulose acetate and cellulose triacetate, polysulfone-based polymers such as polysulfone and polyethersulfone, polyaclyronitrile, polymethyl methacrylate, ethylene-vinyl alcohol copolymers, and the like. Among them, cellulose-based polymers and polysulfone-based polymers are preferable, because the use of them facilitates the manufacturing of selectively permeable separation membranes having water permeability of not lower than 150 mL/m$^2$/hr/mmHg. Cellulose diacetate and cellulose triacetate are preferable among the cellulose-based polymers, because the use of them makes it easy to reduce the thickness of such membranes. The polysulfone-based polymers represent a generic name of resins having sulfone bonds, and preferable examples thereof include, but not limited to, polysulfone resins and polyethersulfone resins having repeating units of the following formulas, which are commercially available with ease:

[Chemical formula 1]

[Chemical formula 2]

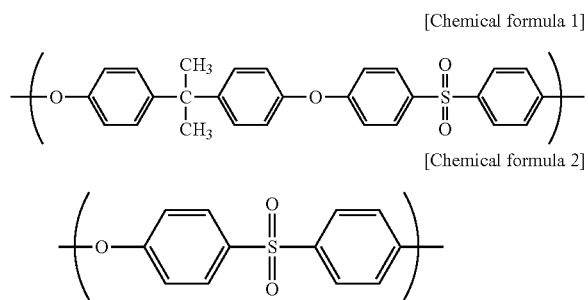

Examples of the hydrophilic polymer to be used in the present invention include, but not limited to, materials such as polyethylene glycol, polyvinyl alcohol, carboxylmethyl cellulose, polyvinyl pyrrolidone and the like, which form micro phase separation structures with the hydrophobic polymers in solutions. In view of safety and cost, the use of polyvinyl pyrrolidone is preferred. Polyvinyl pyrrolidone is a water soluble polymer compound obtained by polymerizing N-vinyl pyrrolidone, and is commercially available under the trade name of LUVITEC™ (BASF), PLASDONE™ (ISP) or PITZCOL™ (DAI-ICHI KOGYO SEIYAKU CO., LTD.). These commercial products have various molecular weights. In general, a polyvinyl pyrrolidone having a low molecular weight is used to efficiently impart hydrophilicity to membranes, and a polyvinyl pyrrolidone having a high molecular weight is used to reduce the amount of an eluted substance. However, a suitable polyvinyl pyrrolidone is selected according to the properties required for a hollow fiber membrane bundle as a final product. Two or more kinds of polyvinyl pyrrolidones which have the same molecular weights or which have difference in molecular weights may be used as a mixture. Otherwise, a commercially available product may be purified to prepare a polyvinyl pyrrolidone having a sharp molecular weight distribution. In the present invention, a polyvinyl pyrrolidone having a high molecular weight is preferably used. The molecular weight of polyvinyl pyrrolidone to be used in the present invention is preferably from 10,000 to 1,200,000, more preferably from 100,000 to 1,200,000, still more preferably from 250,000 to 1,200,000, far still more preferably from 450,000 to 1,200,000, particularly from 600,000 to 1,200,000.

There is no limit in selection of the form of the selectively permeable separation membranes of the present invention. However, the selectively permeable separation membranes are preferable in the form of hollow fiber membranes, because the membrane area per volume can be increased, so that a compact module having a high dialyzing efficiency can be achieved by using such hollow fiber membranes.

The selectively permeable separation membranes and the blood purifier of the present invention can be manufactured by known processes. For example, the hollow fiber type selectively permeable separation membranes are manufactured by extruding a membrane-forming dope from the sheath portion of a double hollow spinneret and extruding an internal injection solution which keeps the hollow portions of the membranes, from the core portion of the spinneret, followed by immersing the semi-solid membrane fibers in a solidifying fluid. Preferably, the hollow fiber membranes manufactured by this method or the like should have inner diameters of 150 to 300 μm and thickness of 10 to 70 μm.

For example, the blood purifier of the present invention is manufactured by inserting a bundle of the hollow fiber membranes into a casing for the blood purifier, pouring a potting agent such as polyurethane in both ends of the membrane bundle to thereby seal both ends thereof, cutting off an excess of the potting agent from both ends thereof to open the end faces of the hollow fiber membranes, and attaching a header to the casing.

In the present invention, the blood purifier comprising the above selectively permeable separation membranes as a main component is sealed in a packaging bag, together with an oxygen scavenger, and is then exposed to a radioactive ray and/or an electron ray for the sterilization thereof. The radioactive ray or the electron ray to be used in the present invention are α-ray, β-ray, γ-ray, electron ray, etc. In view of sterilization efficiency and handling ease, γ-ray or an electron ray is preferably employed. While not limited, the dose of a radioactive ray or an electron ray is such that the sterilization of the blood purifier can be ensured. In general, the dose thereof is from 10 to 30 kGy.

In the present invention, the amount of hydrogen peroxide extracted from the above selectively permeable separation membranes is preferably not larger than 10 ppm, more preferably not larger than 8 ppm, still more preferably not larger than 6 ppm, which is measured after 3 months or longer has passed since the sterilization treatment. When the amount of the extracted hydrogen peroxide is too large, the deterioration of the selectively permeable separation membranes is induced by such hydrogen peroxide, and such deterioration increases the deteriorated substances which are quantitatively determined by UV absorbance. If such deteriorated substances are eluted into the blood during a blood-dialyzing operation, side effects or complications are likely to occur because of such a dialysis therapy over a long period of time.

The regulated available period of blood purifiers for special use as medical devices is generally a period of 3 years counted after the sterilization of the blood purifiers. To guarantee this available period even under a severe environment of the storage and distribution, it is effective to decrease the amount of hydrogen peroxide extracted from the membranes, as mentioned above. In the present invention, it is devised that the amount of hydrogen peroxide extracted from the membranes can be within the above specified range even after 3 to 4 months has passed since the sterilization. By doing so, the deterioration of the materials of the blood purifier can be more effectively prevented during the above available period, preferably during a period of not longer than 5 months, more preferably during a period of not longer than 6 months, still more preferably during a period of not longer than 3 years.

To decrease the amount of extracted hydrogen peroxide to 10 ppm or less, it is preferable to pack the above blood purifier together with an oxygen scavenger in a packaging material capable of shutting out an external air and water vapor under an atmosphere of a room temperature and a relative humidity of exceeding 40% RH, with the proviso that the moisture content of the above selectively permeable separation membranes is maintained at 2.5 mass % or less. Otherwise, it is preferable to pack the blood purifier together with an oxygen scavenger capable of releasing moisture in a packaging material capable of shutting out an external air and water vapor. Hydrogen oxide is formed due to the deterioration of the selectively permeable separation membranes attributed to the exposure to a radioactive ray or an electron ray. An environment around the blood purifier, particularly the selectively permeable separation membranes to be sterilized gives a serious influence on the formation of hydrogen peroxide. That is, the formation of hydrogen peroxide is accelerated in the presence of oxygen, and is inhibited in the presence of water vapor. Therefore, the formation of hydrogen peroxide can be inhibited when the sterilization of the membranes is carried out under the above specified atmosphere. In addition, the sterilization under the above specified atmosphere is effective to decrease the amount of deteriorated substances which is determined by the UV absorbance found in a test regulated in the approved standards for manufacturing dialyzer type artificial kidney devices. Further, the storage of the blood purifier under the above specified atmosphere is effective to suppress an increase in the amount of hydrogen peroxide and an increase in the amount of the deteriorated substances such as an extract, determined by the UV absorbance, both of which tend to increase with time. Accordingly, the reliability in safety of the blood purifier in use for hemocatharsis is markedly improved.

While it is unknown why the deterioration of a hydrophilic polymer (e.g. polyvinyl pyrrolidone) is inhibited by controlling the relative humidity of the inner atmosphere of the packaging bag to not lower than 40% RH (at 25° C.), the following are supposed to inhibit such deterioration.

The deterioration of polyvinyl pyrrolidone is accelerated in the presence of oxygen. In the present invention, the inner atmosphere of the packaging bag is so maintained that the oxidation of polyvinyl pyrrolidone can be inhibited; in other words, the inner atmosphere of the packaging bag is maintained substantially in an anoxia state. However, it is difficult to perfectly control the oxygen concentration in the inner atmosphere of the packaging bag to zero, and a negligibly small amount of oxygen is present in the packaging bag. While no definite reason has been known, the negligibly small amount of oxygen in the packaging bag is allowed to contact polyvinyl pyrrolidone present in the surfaces of the hollow fiber membranes to thereby cause the oxidation of polyvinyl pyrrolidone. This oxidation is supposed to form radicals in a system free of water, and the formed radicals are supposed to attack and deteriorate polyvinyl pyrrolidone. The deterioration of polyvinyl pyrrolidone further facilitates the formation of radicals, with the result that the deterioration of polyvinyl pyrrolidone acceleratedly proceeds and gradually spreads in a whole of the hollow fiber membranes. On the other hand, in a system having water therein, oxidation between oxygen and polyvinyl pyrrolidone takes place without forming any radical. It is supposed that further deterioration of polyvinyl pyrrolidone does not proceed after the oxygen in the system (i.e. the inner atmosphere of a packaging bag) has been consumed. Since polyvinyl pyrrolidone is a highly water-absorbable material, it is sufficient for the system (the inner atmosphere of the bag) to contain a minimum critical amount of water for wetting polyvinyl pyrrolidone. In the present invention, the moisture content of the hollow fiber membranes is sufficient to be 2.5 mass % or so. However, preferably, the relative humidity in the packaging bag is higher than 40% RH in order to prevent the evaporation of water in the hollow fiber membranes, since too low a relative humidity in the packaging bag permits the evaporation of water in the hollow fiber membranes with time.

When polyvinyl pyrrolidone is used in the present invention, it is preferable to use polyvinyl pyrrolidone having a hydrogen peroxide content of 300 ppm or less. By doing so, it becomes easy to decrease the amount of hydrogen peroxide eluted from the resultant hollow fiber membrane bundle to 5 ppm or less. As a result, the quality of the hollow fiber membrane bundle of the present invention can be steady. The hydrogen peroxide content in polyvinyl pyrrolidone as a raw material is preferably 250 ppm or less, more preferably 200 ppm or less, still more preferably 150 ppm or less.

Hydrogen peroxide contained in polyvinyl pyrrolidone for use as a raw material is supposed to be formed in the course of the oxidation and deterioration of polyvinyl pyrrolidone. Therefore, it is effective to take a measure to inhibit the oxidation and deterioration of polyvinyl pyrrolidone in the course of preparation of polyvinyl pyrrolidone, in order to decrease the hydrogen peroxide content to 300 ppm or less. It is also effective and is recommended to take a measure to inhibit the deterioration of polyvinyl pyrrolidone during the transport or the storage of polyvinyl pyrrolidone. For example, polyvinyl pyrrolidone is packed in a bag which is made of an aluminum foil laminate capable of shutting out light and which is charged with an inert gas such as a nitrogen gas; or polyvinyl pyrrolidone is packed together with an oxygen scavenger in such a bag for the storage thereof. The weighing and charging of polyvinyl pyrrolidone which is removed from the opened packaging bag and which is divided into small portions are carried out while the inner atmosphere of the bag being displaced with an inert gas, and polyvinyl pyrrolidone is stored in the bag which is also displaced with an inert gas. Also in the course of manufacturing of a bundle of hollow fiber membranes, it is preferable to displace the inner atmospheres of a supply tank, etc. in a raw material supply system, with an inert gas. Further, a recrystallization method or an extraction method may be employed to decrease the amount of hydrogen peroxide in polyvinyl pyrrolidone.

When the foregoing events are taken into consideration, it is preferable to maintain the moisture content of the membrane and the relative humidity of the atmosphere within the above specified ranges, respectively, while the blood purifier is being sterilized by exposure to a radioactive ray or an electron ray, and it is more preferable to maintain the above conditions even after the exposure of the blood purifier to the radioactive ray or the electron ray.

When the moisture content of the selectively permeable separation membrane exceeds 2.5 mass %, there are likely to arise similar problems to those which occur in the conventional sterilization method under wet conditions: that is, the weight of the blood purifier increases, and bacteria are apt to proliferate. There are also likely to arise some problems when the moisture content of the membranes is controlled before assembling a module: that is, there is a failure in adhesion of a bundle of hollow fiber membranes with an urethane-based resin adhesive or the like for fixing the same in a housing; or an eluate from the membranes tends to increase in amount because of the reaction of the adhesive with water. The lower the moisture content of the selectively permeable separation membranes, the better, because there is less possibility to cause the above-described problems. However, too low a moisture content of the membranes is likely to increase the amount of the eluate from the blood purifier, although why such an event occurs is not well known. Accordingly, the moisture content of the membranes is preferably not lower than 0.5 mass %, more preferably not lower than 0.7 mass %, still more preferably not lower than 1.0 mass %, far more preferably not lower than 1.3 mass %.

In the present invention, the relative humidity is calculated from a partial vapor pressure (p) and a saturated vapor pressure (P) at room temperatures, by the equation: Relative Humidity (%)=p/P×100. This measurement is conducted as follows: the sensor probe of a temperature- and humidity-measuring instrument (ONDOTORI RH Type manufactured by T&D) is inserted into a packaging bag, and then, the bag is sealed to continuously measure the relative humidity within the bag.

In the present invention, the moisture content (mass %) of the hollow fiber membrane can be easily calculated by the following equation:

Moisture content (mass %)=(a−b)/a×100 wherein (a) represents the mass of the hollow fiber membrane before drying, and (b) represents the mass of the bone-dried hollow fiber membrane after drying in an oven at 120° C. for 2 hours. Herein, by adjusting the mass of the hollow fiber membrane (a) to from 1 to 2 g, the hollow fiber membrane can be bone-dried (i.e. a dried state in which the hollow fiber membrane shows no further change in mass) in 2 hours.

In the present invention, the foregoing effects can be exhibited by controlling the relative humidity of the inner atmosphere of the packaging bag, on the prerequisite that the relative humidity around the selectively permeable separation membranes in the blood purifier is maintained within the above specified range. Accordingly, in the blood purifier within the packaging bag, it is preferable to communicate the inner space of the module which holds the selectively permeable separation membranes therein, with an external within the packaging bag. When the opening of the blood purifier is capped, it is preferable to use an air-permeable cap.

To control the relative humidity of the inner atmosphere of the packaging bag to higher than 40% RH at a room temperature, for example, the moisture content of the selectively permeable separation membranes is adjusted to control the above relative humidity; or a gas of which the humidity is controlled is charged in the packaging bag. The gas to be used is preferably an inert gas such as nitrogen, helium, neon, argon or the like in order to inhibit the oxidation and deterioration of the blood purifier as mentioned above. In view of cost-effectiveness and safety in operation, it is preferable to use a nitrogen gas or an argon gas. More preferably, the blood purifier is sealed in the packaging bag, together with an oxygen scavenger and a humectant which releases a moisture content, to thereby control the humidity, as will be described later. In particular, it is preferable to use a moisture release type oxygen scavenger which contains a humectant.

In the present invention, the oxygen scavenger is used in order to lower the oxygen concentration of the ambient atmosphere around the selectively permeable separation membranes as described above. Accordingly, it is preferable to expose the blood purifier in the packaging bag to a radioactive ray or an electron ray, on the condition that the oxygen concentration of the inner atmosphere of the packaging bag has been sufficiently decreased to not higher than 5%, preferably not higher than 1%, more preferably not higher than 0.5%, still more preferably not higher than 0.1%. For example, when the gas in the inner atmosphere of the bag is an air, the oxygen concentration of the inner atmosphere of the bag usually decreases to 0.1% or lower after 48 hours or so has passed since the blood purifier was sealed in the packaging bag. Accordingly, preferably, it is 2 days after the sealing of the bag that the blood purifier in the packaging bag should be exposed to a radioactive ray or an electron ray. In this regard, too long a time interval between the sealing of the bag and the sterilization of the blood purifier is likely to permit the proliferation of bacteria, and thus, the sterilization of the blood purifier should be done within 10 days, preferably 7 days, more preferably 5 days after the sealing of the bag.

The oxygen scavenger to be used in the present invention is not limited, in so far as it can scavenge oxygen. Examples of the oxygen scavenger of the present invention are such oxygen scavengers that contain, as main oxygen-absorbing agents, sulfite, hydrogensulfite, dithionite, hydroquinone, catechol, resorcinol, pyrogallol, gallic acid, rongalite, ascorbic acid and/or a salt thereof, sorbose, glucose, lignin, dibutylhydroxytoluene, dibutylhydroxyanisole, ferrous salt, metal powder (e.g. iron powder, etc.) and the like. The oxygen scavenger may be appropriately selected from these materials for use. An oxygen scavenger mainly comprising metal powder, if needed, may contain, as an oxidation catalyst, one or more compounds selected from halogenated metal compounds such as sodium chloride, potassium chloride, magnesium chloride, calcium chloride, aluminum chloride, ferrous chloride, ferric chloride, sodium bromide, potassium bromide, magnesium bromide, calcium bromide, iron bromide, nickel bromide, sodium iodide, potassium iodide, magnesium iodide, calcium iodide, iron iodide, etc. If needed, the oxygen scavenger may contain a moisture or a moisture-imparting agent. As described above, it is preferable in the present invention to control the relative humidity in the inner atmosphere of the packaging bag to higher than 40% RH at a room temperature. Thus, to impregnate the oxygen scavenger with a moisture or to add a moisture-imparting agent to the oxygen scavenger is recommended as a preferable method. Further, a separate moisture-imparting agent may be used together with a general-purpose oxygen scavenger to scavenge the oxygen in the packaging bag and to control the humidity of the inner atmosphere of the packaging bag. Additionally, other functional fillers such as a deodorant may be included in the packaging bag. The form of the oxygen scavenger is not limited, and it may be in the form of powder, particles, mass or sheet; or it may be a sheet- or film-shaped oxygen scavenger obtained by dispersing an oxygen absorber composition in a thermoplastic resin.

Preferably, the packaging bag to be used in the present invention is made of an oxygen- or water vapor-impermeable material. This is because the use of such a material is effective to maintain the humidity and the oxygen concentration of the sealed atmosphere within the above-specified ranges over a long period of time, to thereby inhibit the aged deterioration of the components of the blood purifier before and after the exposure, and to thereby inhibit an increase in the amount of the extract from the blood purifier. Accordingly, the oxygen permeability of the material for the packaging bag is preferably at most 1 cm$^3$/(m$^2 \cdot$24 hr·atm) (20° C., 90% RH), and the water vapor permeability thereof is preferably at most 5 g/(m$^2 \cdot$24 hr·atm) (40° C., 90% RH).

The oxygen permeability of the material for the packaging bag is more preferably at most 0.9 cm$^3$/(m$^2$·24 hr·atm) (20° C., 90% RH), still more preferably at most 0.8 cm$^3$/(m$^2$·24 hr·atm) (20° C., 90% RH), far more preferably at most 0.7 cm$^3$/(m$^2$·24 hr·atm) (20° C., 90% RH). The water vapor permeability thereof is more preferably at most 4 g/(m$^2$·24 hr·atm) (40° C., 90% RH), still more preferably at most 3 g/(m$^2$·24 hr·atm) (40° C., 90% RH), far more preferably at most 2 g/(m$^2$·24 hr·atm) (40° C., 90% RH).

The material and structure of the packaging bag to be used in the present invention may be optionally selected, so long as the above characteristics are satisfied. Preferable examples of the material for the packaging bag are oxygen- and water vapor-impermeable materials such as an aluminum foil, aluminum-deposited film, inorganic oxide-deposited film of silica and/or alumina, vinylidene chloride type polymer composite film and the like. The sealing method for the packaging bag also may be optionally selected. For example, the packaging bag may be sealed by any of the heat sealing method, impulse heat sealing method, fusion sealing method, frame sealing method, ultrasonic sealing method, high frequency sealing method and the like. Thus, preferable as the material for the packaging bag is a composite material of a film having a sealing property and any of the above impermeable materials. Particularly preferable is a laminate sheet comprising a structural layer of an aluminum foil capable of substantially shutting out an oxygen gas and a water vapor, an outer layer of a polyester film, an intermediate layer of an aluminum foil, and an inner layer of a polyethylene film, since this laminate sheet has both of impermeability and a heat sealing property.

Preferably, the blood purifier of the present invention should satisfy the following amounts of extracts therefrom when used for hemodialysis.
(1) The UV absorbance of an extract at 220 to 350 nm according to the approved standards for manufacturing dialyzer type artificial kidney devices is lower than 0.10.
(2) The amount of a hydrophilic polymer extracted from the blood purifier, using a 40% aqueous ethanol solution is not larger than 2.0 mg/m$^2$ per 1.0 m$^2$ of a surface of the membrane on the treated fluid-contacting side.
(3) The amount of hydrogen peroxide in the extract from the blood purifier according to the approved standards for manufacturing dialyzer type artificial kidney devices is not larger than 10 ppm.

In the known technologies, keen attentions have been paid to the amounts of the extracts (1) and (2) as the values found just after the sterilizing treatment, however, quite no attention is paid to increases in the amounts of the above extracts with time after the sterilizing treatment. The amounts of hydrogen peroxide (3) found immediately after the exposure, and so on, have been firstly made clear by the present inventors. The present invention, accomplished by paying keen attentions to these novel events and elucidating these events, will significantly contribute to remarkable improvement on reliability in safety of the blood purifier.

EXAMPLES

Hereinafter, the effects of the present invention will be described by Examples thereof, which, however, should not be construed as limiting the scope of the present invention in any way. The physical properties of the following Examples are evaluated as follows. In Examples, the notation "ND" means "not detected".

1. Calculation of the Area of Membranes

The area of membranes in a dialyzer was calculated by the following equation, based on the inner diameter of the hollow fiber membrane:

$$A(m^2) = n \times \pi \times d \times L$$

[in the equation, n represents the number of hollow fiber membranes in the dialyzer; π represents the ratio of the circumference of a circle to its diameter; d represents the inner diameter (m) of the hollow fiber membrane; and L represents the effective length (m) of the hollow fiber membranes in the dialyzer].

2. UV Absorbance (at 220 to 350 nm) According to Approved Standards for Manufacturing Dialyzer Type Artificial Kidney Devices Extraction and measurement were conducted according to the methods regulated in the approved standards for manufacturing dialyzer type artificial kidney devices. A sample of hollow fiber membranes (1 g) was admixed with pure water (100 mg), and the mixture was subjected to extraction at 70° C. for one hour to prepare a test solution. Then, the UV absorbance of this test solution at a wavelength of 220 to 350 nm was measured. According to the above standard, the maximum absorbance is regulated to lower than 0.1.

3. Amount of Hydrophilic Polymer Extracted with 40% Aqueous Ethanol Solution

A case of polyvinyl pyrrolidone (PVP) as an example of hydrophilic polymers is described.

A module with its passage on the dialyzing fluid side closed was connected to a silicone tube circuit, and pure water was allowed to pass through the passage on the blood side of the module to fill both the module and the circuit with pure water. After that, a 40 v/v % ethanol solution was allowed to pass through the passage on the blood side of the module at a flow rate of 150 ml/min., and 100 ml of the same solution was discharged from the outlet of the circuit. The inlet and the outlet of the passage on the blood side were closed with forceps, and the passage on the dialyzing fluid side was successively filled with the 40 v/v % ethanol solution, and was again closed. The 40 v/v ethanol solution, the circuit and the module were all controlled to 40° C., and the ethanol solution was circulated at a flow rate of 150 ml/min. Sixty minutes after, all the fluids in the circuit and the module were discharged and collected together with the circulating fluid to measure the volume of the mixture. The fluid on the dialyzing fluid side was separately collected to measure its volume. The PVP contents of the respective fluids were measured according to the following procedure. A sample of each fluid (2.5 ml) was admixed with 0.2 mol/L citric acid (1.25 ml), and the mixture was stirred. Then, 0.006N iodine (500 μL) was added, and the resulting mixture was stirred and was left to stand at a room temperature for 10 minutes. After that, the absorbance of the resultant solution was measured. When the PVP content of the solution was high, the solution was diluted 10 or 100 times larger in volume, and then, the PVP content was measured. The PVP content in the sample was calculated from an analytical curve prepared under the same conditions, to thereby calculate the amount of eluted PVP (mg/m$^2$) per module (1.0 m$^2$).

4. Determination of Hydrogen Peroxide

A fluid (2.6 mL) extracted from the membrane by the method regulated in the UV absorptionmetry (at 220 to 350 nm) according to the approved standards for manufacturing dialyzer type artificial kidney devices was admixed with an ammonium chloride buffer solution (pH 8.6) (0.2 mL) and a 0.4 mM coloring reagent (0.2 mL) which was prepared by mixing an aqueous solution of titanium tetrachloride (TiCl$_4$)

and hydrogen chloride with an aqueous solution of 4-(2-pyridylazo)resorcinol and Na salt in equivalent amounts in molar ratio. The mixture was heated at 50° C. for 5 minutes, and then was cooled to a room temperature and was subjected to an absorptionmetry at 508 nm. Determination was made by using an analytical curve which was found by the measurement under the same conditions.

5. Oxygen Concentration in Packaging Bag

The measurement was conducted by gas chromatography, using a column filled with a molecular sieve (13X-S mesh 60/80 manufactured by GL Science), an argon gas as a carrier gas, and a detector of heat-conduction system. An analysis was made at a column temperature of 60° C. A gas within a packaging bag was collected by directly pricking the closed packaging bag with a syringe needle.

6. Oxygen Permeability of Packaging Material

An oxygen permeability-measuring apparatus (OX-TORAN 100 manufactured by Modern Controls) was used to measure the oxygen permeability of the material of the packaging bag at 20° C. and 90% RH.

7. Water Vapor Permeability of Packaging Material

A water vapor permeability-measuring apparatus (PARMATRAN-W manufactured by Modern Controls) was used to measure the water vapor permeability of the material of the packaging bag at 40° C. and 90% RH.

8. Moisture Content of Hollow Fiber Membrane

To find a moisture content (mass %) of a hollow fiber membrane, the mass (a) of the hollow fiber membrane before dried and the mass (b) of the same hollow fiber membrane after dried at 120° C. in an oven for 2 hours (bone-dried) were measured. The moisture content was calculated by the following equation:

Moisture content (mass %)=$(a-b)/a \times 100$ wherein, if (a) is from 1 to 2 g, the hollow fiber membrane could be bone-dried in 2 hours (if bone-dried, the membrane shows no further change in mass).

Example 1

A spinning dope was prepared from polyethersulfone (PES) (4800P, manufactured by Sumitomo Chemical Company, Limited) (17.5 mass %), polyvinyl pyrrolidone (PVP) (K90 manufactured by BASF) (3.5 mass %) as a hydrophilicity-imparting agent, water (1.0 mass %) as a non-solvent, triethylene glycol (TEG manufactured by Mitsubish Chemical Corporation) (31.2 mass %) and dimethylacetamide (DMAc manufactured by MITSUI CHEMICALS, INC.) (46.8 mass %). The spinning dope was extruded from the outer slit of a double spinneret maintained at 45° C., and water as an inner solution was extruded from the inner injection hole of the double spinneret. The resulting semi-solid hollow fiber was allowed to pass through an air gap with a length of 600 mm at a spinning rate of 60 m/minute, and was then dipped in a solidifying bath of 70° C. (DMAc:TEG:water=6:4:90). After that, the hollow fiber was washed with pure water of 45° C. for one minute followed by pure water of 80° C. for 90 seconds, and then was wound onto a hank. Thus, the hollow fiber membrane with an inner diameter of 198.8 μm and a thickness of 29.5 μm was obtained.

About 10,000 hollow fiber membranes thus obtained were inserted into a polyethylene pipe, which was then cut with a predetermined length. After that, the hollow fiber membranes in the pipe were dried in a hot air drier of 40° C. until the moisture content in the hollow fiber membranes became 1.5 mass %. Thus, a bundle of the hollow fiber membranes was obtained.

The bundle was packed in a casing at a packing ratio of 60 vol %, and the end portions of the bundle were bonded with an urethane resin. After that, the resin was cut out to finish a module of which the hollow fiber membrane area was 1.5 m². This module was sealed in a packaging bag together with a general-purpose iron powder type oxygen scavenger. In this regard, the packaging bag was made of an aluminum lamination sheet which had an outer layer of a polyester film, an intermediate layer of an aluminum foil and an inner layer of a polyethylene film and which had an oxygen permeability of 0.5 cm³/(m²·24 hr·atm) and a water vapor permeability of 0.5 g/(m²·24 hr·atm). The relative humidity of the internal atmosphere of the packaging bag was adjusted to 70% RH with a humidifying nitrogen. After 48 hours had passed since the sealing, the module in the packaging bag was exposed to a γ-ray at a dose of 20 kGy for the sterilization thereof. Thus, a blood purifier package was obtained. The resultant blood purifier package was then stored at a room temperature. The humidity and oxygen concentration of the internal atmosphere of the packaging bag, the moisture content of the hollow fiber type selectively permeable separation membranes, the UV absorbance of the blood purifier in an elution test, the amount of an extract from the blood purifier with ethanol, and the amount of hydrogen peroxide from the blood purifier were measured immediately after the sterilization, and one month and three months after the sterilization, respectively. The results are shown in Tables 1 and 2.

Comparative Example 1

A blood purifier package was obtained in the same manners as in Example 1, except that the internal atmosphere of a packaging bag was not controlled. The results of the evaluation of the obtained blood purifier, which changed with time, are shown in Tables 1 and 2. Since the humidity in the system was too low, it was observed that the amounts of the eluate and hydrogen peroxide increased with time.

Comparative Example 2

A blood purifier package was obtained in the same manners as in Example 1, except that no oxygen scavenger was used. The results of the evaluation of the obtained blood purifier, which changed with time, are shown in Tables 1 and 2. Since the oxygen concentration in the system was high, it was supposed that the amount of hydrogen oxide increased since oxygen radicals formed due to the γ-ray exposure. It was also supposed that the deterioration and decomposition of the hydrophilic polymer was further accelerated.

Example 2

A blood purifier package was obtained in the same manners as in Example 1, except that the moisture content of the hollow fiber membrane bundle was decreased to 0.7 mass % by intensifying the drying of the hollow fiber membrane bundle, that the humidity of the internal atmosphere of a packaging bag was not controlled, and that a moisture release type oxygen scavenger was used. The results of the evaluation of the obtained blood purifier, which changed with time, are shown in Tables 1 and 2.

Comparative Example 3

A blood purifier package was obtained in the same manners as in Example 1, except that the humidities of the selectively permeable separation membranes and the internal atmosphere of a packaging bag were not controlled, and that no oxygen scavenger was used. The results of the evaluation of the obtained blood purifier, which changed with time, are shown in Tables 1 and 2. Since the moisture content and the humidity were insufficient, the deterioration and decomposition of the hydrophilic polymer was accelerated, and the amount of the eluate increased with time.

Comparative Example 4

A blood purifier package was obtained in the same manners as in Example 1, except that a blood purifier was packed in a packaging bag having an oxygen permeability and a water vapor permeability. The resultant blood purifier package was stored under the same conditions as in Example 1. The results of the evaluation of the obtained blood purifier, which changed with time, are shown in Tables 1 and 2. Since the packaging bag could not shut out oxygen and water vapor, external oxygen and water vapor permeated the system, and the influences thereof accelerated the deterioration and decomposition of the hydrophilic polymer, and the amount of an eluate from the blood purifier increased with time.

Example 3

A blood purifier package was obtained in the same manners as in Example 2, except that the same general-purpose oxygen scavenger as that used in Example 1 was used, and that the blood purifier was sealed in a packaging bag together with a humectant which was obtained by sealing zeolite powder having adsorbed water in a humidity permeable packaging material. The results of the evaluation of the obtained blood purifier, which changed with time, are shown in Tables 1 and 2.

Example 4

A blood purifier package was obtained in the same manners as in Example 1, except that an electron ray exposure apparatus with an accelerated voltage of 5,000 KV was used instead of the γ-ray. The results of the evaluation of the obtained blood purifier, which changed with time, are shown in Tables 1 and 2.

TABLE 1

|  | Just after sterilization | | | 1 month after sterilization | | | 3 months after sterilization | | |
| --- | --- | --- | --- | --- | --- | --- | --- | --- | --- |
|  | Moisture content (mass %) | Relative humidity (% RH) | Oxygen concentration (%) | Moisture content (mass %) | Relative humidity (% RH) | Oxygen concentration (%) | Moisture content (mass %) | Relative humidity (% RH) | Oxygen concentration (%) |
| Ex.1 | 1.9 | 72 | ND | 1.9 | 72 | ND | 1.9 | 72 | ND |
| Ex.2 | 1.8 | 71 | ND | 1.9 | 70 | ND | 1.9 | 70 | ND |
| Ex.3 | 2.0 | 70 | ND | 1.9 | 68 | ND | 2.0 | 68 | ND |
| Ex.4 | 1.7 | 69 | ND | 1.7 | 68 | ND | 1.8 | 69 | ND |
| C.Ex.1 | 0.5 | 35 | ND | 0.4 | 36 | ND | 0.5 | 35 | ND |
| C.Ex.2 | 1.9 | 70 | 24 | 1.9 | 70 | 24 | 2.0 | 68 | 25 |
| C.Ex.3 | 0.5 | 64 | 25 | 0.5 | 42 | 25 | 0.5 | 33 | 25 |
| C.Ex.4 | 2.0 | 35 | 25 | 1.8 | 35 | 24 | 1.7 | 35 | 25 |

TABLE 2

|  | Just after sterilization | | | 1 month after sterilization | | | 3 months after sterilization | | |
| --- | --- | --- | --- | --- | --- | --- | --- | --- | --- |
|  | UV | Extract from EtOH (mg/m$^2$) | $H_2O_2$ (ppm) | UV | Extract from EtOH (mg/m$^2$) | $H_2O_2$ (ppm) | UV | Extract from EtOH (mg/m$^2$) | $H_2O_2$ (ppm) |
| Ex.1 | 0.04 | 1.5 | 1 | 0.04 | 1.4 | 0 | 0.05 | 1.5 | 2 |
| Ex.2 | 0.05 | 1.4 | 1 | 0.04 | 1.4 | 1 | 0.04 | 1.4 | 1 |
| Ex.3 | 0.04 | 1.5 | 0 | 0.05 | 1.5 | 0 | 0.04 | 1.4 | 1 |
| Ex.4 | 0.05 | 1.5 | 1 | 0.04 | 1.4 | 0 | 0.05 | 1.3 | 1 |
| C.Ex.1 | 0.09 | 1.8 | 5 | 0.11 | 2.2 | 10 | 0.15 | 2.8 | 15 |
| C.Ex.2 | 0.84 | 2.1 | 73 | 0.96 | 2.4 | 92 | 1.03 | 2.5 | 87 |
| C.Ex.3 | 1.07 | 2.5 | 142 | 1.33 | 3.0 | 176 | 1.41 | 3.6 | 203 |
| C.Ex.4 | 0.22 | 2.2 | 18 | 0.37 | 3.7 | 29 | 0.42 | 4.1 | 33 |

INDUSTRIAL APPLICABILITY

The blood purifier, sterilized by exposure to a radioactive ray and/or an electron ray, according to the present invention shows a decreased amount of hydrogen peroxide which is extracted therefrom and which changes in amount with time during and after the above exposure, and further, formation of a variety of extracted substances attributed to the deterioration of the selectively permeable separation membranes due to the hydrogen peroxide is inhibited. Therefore, the reliability in safety of the blood purifier in use for a hemocathartic therapy is markedly improved, and therefore, the blood purifier of the present invention will significantly contribute to this industry.

The invention claimed is:

1. A blood purifier comprising selectively permeable separation membranes as a main component, characterized in that the amount of hydrogen peroxide which is extracted from the selectively permeable separation membranes removed from the blood purifier after 3 months or longer has passed since the sterilization of the blood purifier by exposure to a radioactive ray and/or an electron ray is not larger than 10 ppm, wherein the selectively permeable separation membranes comprise a polysulfone-based polymer containing polyvinyl pyrrolidone, and wherein the blood purifier is sealed together with an oxygen scavenger capable of releasing moisture in a packaging material capable of shutting out external air and water vapor, the atmosphere inside the packaging material has a relative humidity of higher than 68% RH at room temperature, and the blood purifier has been sterilized by exposure of the blood purifier within the sealed packaging material to a radioactive ray, an electron ray, or both a radioactive ray and an electron ray.

2. The blood purifier according to claim 1, wherein the selectively permeable separation membranes have a moisture content of not higher than 2.5 mass %.

3. A blood purifier package comprising the blood purifier of claim 1 packed in a packaging material.

4. The blood purifier package according to claim 3, wherein the oxygen permeability of the packaging material is not higher than 1 $cm^3/(m^2 \cdot 24\ hr \cdot atm)$ (20° C. and 90% RH).

5. The blood purifier package according to claim 3, wherein the water vapor permeability of the packaging material is not higher than 5 $g/(m^2 \cdot 24\ hr \cdot atm)$ (40° C. and 90% RH).

6. The blood purifier package according to claim 4, wherein the water vapor permeability of the packaging material is not higher than 5 $g/(m^2 \cdot 24\ hr \cdot atm)$ (40° C. and 90% RH).

7. The blood purifier package according to claim 3, wherein the selectively permeable separation membranes have a moisture content of not higher than 2.5 mass %.

* * * * *